(12) United States Patent
Yoshimuta

(10) Patent No.: US 8,581,201 B2
(45) Date of Patent: Nov. 12, 2013

(54) POWER SUPPLY APPARATUS FOR A DETECTOR, AND A LIGHT OR RADIATION DETECTION SYSTEM HAVING THE SAME

(75) Inventor: Toshinori Yoshimuta, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 973 days.

(21) Appl. No.: 12/669,390

(22) PCT Filed: Jul. 17, 2007

(86) PCT No.: PCT/JP2007/064075
§ 371 (c)(1),
(2), (4) Date: Jan. 15, 2010

(87) PCT Pub. No.: WO2009/011027
PCT Pub. Date: Jan. 22, 2009

(65) Prior Publication Data
US 2010/0187430 A1   Jul. 29, 2010

(51) Int. Cl.
*G01T 1/24* (2006.01)
(52) U.S. Cl.
USPC .................................. 250/370.09; 250/370.08
(58) Field of Classification Search
USPC ..................................................... 250/370.09
See application file for complete search history.

(56) References Cited

U.S. PATENT DOCUMENTS

| | | | |
|---|---|---|---|
| 3,906,233 A * | 9/1975 | Vogel | 378/65 |
| 6,847,404 B1 * | 1/2005 | Jackson et al. | 348/378 |
| 7,131,013 B2 * | 10/2006 | Sasakura et al. | 713/300 |

FOREIGN PATENT DOCUMENTS

| | | |
|---|---|---|
| JP | 2002-191586 A | 7/2002 |
| JP | 2003-258218 A | 9/2003 |
| JP | 2005-109751 A | 4/2005 |
| JP | 2005-118348 A | 5/2005 |

OTHER PUBLICATIONS

International Search Report for the Application No. PCT/JP2007/064075 mailed Oct. 23, 2007.

* cited by examiner

*Primary Examiner* — Marcus Taningco
(74) *Attorney, Agent, or Firm* — Cheng Law Group, PLLC

(57) ABSTRACT

A power supply apparatus for a detector of this invention provides a plurality of power supplies for the detector for detecting light or radiation, and includes a power output device capable of individually outputting the plurality of power supplies to be provided for the detector, a detection device for detecting a power supply state of a utility power source, a control device for carrying out an abnormal stopping process to stop the power supplies at the power output device in a predetermined order upon determination based on a result of detection by the detection device that an abnormality has occurred, and an electric storage device for supplying electric power to the control device, when the control device determines that an abnormality has occurred, to permit the control device to carry out the abnormal stopping process. Thus, without having a large-scale uninterruptible power supply system, the detector can be protected even when the electric power supply state from the utility power source becomes abnormal.

26 Claims, 5 Drawing Sheets

POWER SUPPLY APPARATUS FOR A DETECTOR, AND A LIGHT OR RADIATION DETECTION SYSTEM HAVING THE SAME

TECHNICAL FIELD

This invention relates to a power supply apparatus for a detector for supplying power to a detector which detects light or radiation used in the medical field, and in industrial fields such as for nondestructive testing, RI (Radio isotope) inspection and optical inspection, and to a light or radiation detection system having the same.

BACKGROUND ART

Conventionally, a flat panel detector (hereinafter simply called "FPD") is used as a detector for detecting light or radiation. The FPD includes a semiconductor layer, an application electrode, an active matrix substrate, a driver and a processor. The semiconductor layer converts light or radiation information into charge information. The application electrode is formed on a surface of the semiconductor layer to apply a high voltage power supply to the semiconductor layer. The active matrix substrate has a plurality of switching elements to read the charge information from the semiconductor layer. The driver drives this active matrix substrate for reading. The processor amplifies and digitizes the charge information read from the active matrix substrate. A power supply apparatus is connected to the FPD, and various power supplies are provided from the power supply apparatus.

Reference is made to FIG. 5. FIG. 5 is a view showing an outline construction of a power supply apparatus in a conventional example. The power supply apparatus 61 outputs two or more types of driving power supplies V1 provided for the driver, a plurality of processing power supplies V2 provided for the processor, and a high voltage power supply V3 provided for the application electrode. This power supply apparatus 61 includes a power output unit 63 formed of a plurality of output circuits 64 arranged on lines of the various power supplies V1, V2 and V3, respectively, to output the various power supplies V1, V2 and V3 individually. The power output unit 63 is controlled by a controller 65.

An operating unit 71 is connected to the power supply apparatus 61. The operating unit 71 is formed of a computer having an input device such as a keyboard. When the user operates this operating unit 71, the operating unit 71 receives instructions to an FPD 75, and gives the received instructions to the controller 65. A utility power source 79 is connected to these power supply apparatus 61 and operating unit 71 through an uninterruptible power supply system (hereinafter simply called "UPS") 77.

In the conventional example constructed in this way, the power supply apparatus 61 and operating unit 71 are operable with electric power supplied from the utility power source 79, and the UPS 77 accumulates electric power. When the user inputs startup instructions to the operating unit 71, the controller 65 outputs the various power supplies V1, V2 and V3 in a predetermined order. Consequently, the power supplies are successively provided for the driver and the like of the FPD 75. When stop instructions are inputted to the operating unit 71, the controller 65 stops the output of the various power supplies in a predetermined order. Consequently, the power supplies for the driver and the like of the FPD 75 stop. The predetermined orders are decided for the purpose of protection of each circuit such as the driver of the FPD 75.

When an instantaneous interruption or power failure occurs and the voltage of the utility power source 79 falls, the UPS 77 supplies electric power to the power supply apparatus 61 and operating unit 71. Consequently, the various power supplies are continuously provided for the FPD 75 from the power supply apparatus 61. The operating unit 71 also continues its operation to be able to receive instructions from the user. Therefore, when the user inputs stop instructions to the operating unit 71, the FPD 75 can be stopped normally. Thus, even when the utility power source 79 undergoes a voltage drop, the power supplies are not stopped in an order other than the predetermined order, such as the output of the various power supplies to the FPD 75 stopping all at once. Therefore, the FPD 75 can be protected from damage, destruction or breakdown (see Patent Document 1. for example).

[Patent Document 1]
Japanese Unexamined Patent Publication No. 2003-258218

DISCLOSURE OF THE INVENTION

Problem to be Solved by the Invention

However, the conventional example with such construction has the following drawback.

That is, the conventional example has an inconvenience that the UPS 77 is large-scaled which results in high cost. That is, it is desirable that the UPS 77 accumulates at least electric energy for operating the FPD 75 and operating unit 71 for several minutes. However, the UPS 77 having such an amount of accumulation of electricity becomes large-scaled, and it is difficult to secure its storage space. Such large-capacity UPS 77 is expensive and is a cause of cost increase.

This invention has been made having regard to the state of the art noted above, and its object is to provide a power supply apparatus for a detector, and a light or radiation detection system having the same, which can protect the detector even when a state of electric power supply from a utility power source becomes abnormal, without requiring a large-capacity uninterruptible power supply system.

Means for Solving the Problem

To fulfill this object, this invention provides the following construction.

A power supply apparatus for a detector of this invention, for providing a plurality of power supplies for a light or radiation detecting detector having a semiconductor layer for converting light or radiation information into charge information, an active matrix substrate having a plurality of switching elements for reading the charge information from the semiconductor layer, and a driving device for driving the active matrix substrate for reading, comprises a power output device capable of individually outputting the plurality of power supplies to be provided for the detector; a detection device for detecting a power supply state of a utility power source for operating the apparatus; a control device for carrying out an abnormal stopping process to stop the power supplies at the power output device in a predetermined order upon determination based on a result of detection by the detection device that an abnormality has occurred; and an electric storage device for supplying electric power to the control device, when the control device determines that an abnormality has occurred, to permit the control device to carry out the abnormal stopping process.

According to the power supply apparatus for a detector of this invention, with the detection device provided, the control device can directly monitor the power supply state of the utility power source. Since the electric storage device is provided for supplying electric power to the control device when the control device determines that an abnormality has occurred, the control device can appropriately carry out the abnormal stopping process for stopping the detector. This can prevent destruction, damage or breakdown of the detector. Since the electric storage device does not supply electric power to the entire power supply apparatus for a detector, the electric energy the electric storage device should accumulate is an extremely small amount. Therefore, a large-capacity uninterruptible power supply system is not required, whereby the power supply apparatus for a detector can be constructed at low cost. The control device automatically carries out the abnormal stopping process when the control device determines that an abnormality has occurred, and thus a manual operation is not required.

In the power supply apparatus for a detector of this invention, it is preferred that the electric storage device is capable of continuing to supply electric power to the control device at least over a time required for the abnormal stopping process. The control device can carry out the abnormal stopping process reliably.

In the power supply apparatus for a detector of this invention, it is preferred that the time required for the abnormal stopping process is at most one second. Since the abnormal stopping process is completed in a short time, the power supplies at the power output device can be stopped in a predetermined order.

In the power supply apparatus for a detector of this invention, it is preferred that the electric storage device is capable of storing electric power to be consumed by the control device at least during the abnormal stopping process. The control device can carry out the abnormal stopping process conveniently.

In the power supply apparatus for a detector of this invention, it is preferred that the electric storage device is an electric double layer capacitor. The electric storage device formed of an electric double layer capacitor can be charged and discharged quickly. The electric double layer capacitor can be charged and discharged only by time constant, and does not require a special circuit for charging and discharging unlike a battery. Since the electric double layer capacitor has a long life, it provides for excellent maintainability.

In the power supply apparatus for a detector of this invention, it is preferred that the electric double layer capacitor has a capacitance of at least 1000 µF. The control device is fully permitted to carry out the abnormal stopping process, and the electric storage device can be made very compact.

In the power supply apparatus for a detector of this invention, it is preferred that the detection device is arranged to detect a voltage of the utility power source. The power supply state of the utility power source can be detected properly.

In the power supply apparatus for a detector of this invention, it is preferred that the control device is arranged to determine that an abnormality has occurred, when the voltage detected by the detection device falls below a reference value. The control device can properly determine whether an abnormality has occurred.

In the power supply apparatus for a detector of this invention, it is preferred that the power supplies the power output device is capable of individually outputting include a plurality of driving power supplies to be provided for the driving device; and in the abnormal stopping process, a driving power supply of highest voltage among the driving power supplies is stopped before the other driving power supplies. This can conveniently prevent destruction and damage of the driving device in time of the abnormal stopping process.

In the power supply apparatus for a detector of this invention, it is preferred that the power supplies the power output device is capable of individually outputting include a plurality of driving power supplies to be provided for the driving device; the driving power supplies further include an ON-state voltage power supply for applying an ON-state voltage to set the switching elements to ON state; and in the abnormal stopping process, the ON-state voltage power supply is stopped before the other driving power supplies. By stopping the ON-state voltage power supply of relatively high voltage before the other driving power supplies, the driving device can be protected conveniently in time of the abnormal stopping process.

In the power supply apparatus for a detector of this invention, it is preferred that the ON-state voltage of the ON-state voltage power supply is higher than voltages of the other driving power supplies. The driving device can be protected effectively.

In the power supply apparatus for a detector of this invention, it is preferred that the driving device includes a drive circuit for switching provision and stopping of the ON-state voltage power supply for the switching elements, and a drive control circuit for controlling switching of the drive circuit; the ON-state voltage power supply is inputted to the drive circuit; and the other driving power supplies are inputted to one of the drive circuit and the drive control circuit. The drive circuit and drive control circuit can be protected effectively.

In the power supply apparatus for a detector of this invention, it is preferred that the drive circuit comprises integrated circuits. The drive circuit can be formed conveniently.

In the power supply apparatus for a detector of this invention, it is preferred that specifications of the integrated circuits provide that the other power supplies should be stopped after stopping the ON-state voltage power supply when stopping the plurality of power supplies to the integrated circuits. Where the integrated circuits with specifications defined in this way are used, the integrated circuits are effectively protected by carrying out the abnormal stopping process.

In the power supply apparatus for a detector of this invention, it is preferred that the detector includes a processing device for processing the charge information read by the active matrix substrate; the power supplies the power output device is capable of individually outputting include a plurality of processing power supplies to be provided for the processing device; and in the abnormal stopping process, the ON-state voltage power supply is stopped before all the processing power supplies. By stopping the ON-state voltage power supply before the processing power supplies, the driving device and processing device can be protected conveniently in time of the abnormal stopping process.

In the power supply apparatus for a detector of this invention, it is preferred that the processing device includes at least amplifier circuits for amplifying the charge information, and an analog-to-digital converter circuit for digitizing output of the amplifier circuits; and the processing power supplies are inputted to the amplifier circuits and the analog-to-digital converter circuit, respectively. The amplifier circuits and the analog-to-digital converter circuit can be protected conveniently in time of the abnormal stopping process.

In the power supply apparatus for a detector of this invention, it is preferred that the power supplies the power output device is capable of individually outputting include a high voltage power supply for applying a high voltage to the semiconductor layer; and in the abnormal stopping process, the high voltage power supply is stopped first among the power supplies the power output device is capable of individually outputting. The switching elements can be protected conveniently in time of the abnormal stopping process.

A light or radiation detection system of this invention, preferably, has a detector powered by the power supply apparatus for a detector for detecting light or radiation; wherein the detector comprises a semiconductor layer for converting light or radiation information into charge information; an active matrix substrate having a plurality of switching elements for reading the charge information from the semiconductor layer; and a driving device for driving the active matrix substrate for reading. According to the light or radiation detection system of this invention, destruction, damage or breakdown of the detector are never prevented in time of the abnormal stopping process.

A light or radiation detection system of this invention, preferably, has a detector powered by the power supply apparatus for a detector for detecting light or radiation; wherein the detector comprises a semiconductor layer for converting light or radiation information into charge information; an active matrix substrate having a plurality of switching elements for reading the charge information from the semiconductor layer; and a driving device for driving the active matrix substrate for reading; wherein the driving device includes a drive circuit for switching provision and stopping of the ON-state voltage power supply for the switching elements; and a drive control circuit for controlling switching of the drive circuit; and wherein the drive circuit comprises integrated circuits; and specifications of the integrated circuits provide that the other power supplies should be stopped after stopping the ON-state voltage power supply when stopping the plurality of power supplies to the integrated circuits. The drive circuit formed of the integrated circuits can be protected effectively in time of the abnormal stopping process.

It is preferred that the light or radiation detection system of this invention is used exclusively for radiography. In the case of exclusive use for radiography, the light or radiation detection system is not continuously used such as in a surgical operation, insertion of a catheter or IVR. Thus, the control device, when it determines that an abnormality has occurred, can automatically carry out the abnormal stopping process without causing any inconvenience.

Effects of the Invention

According to the power supply apparatus for a detector of this invention, with the detection device provided, the control device can monitor the power supply state of the utility power source. Since the electric storage device is provided for supplying electric power to the control device when the control device determines that an abnormality has occurred, the control device can appropriately carry out the abnormal stopping process for stopping the detector. This can prevent destruction or breakdown of the detector. Since the electric storage device does not supply electric power to the entire power supply apparatus for a detector, the electric energy the electric storage device should secure can be greatly reduced. Therefore, a large-capacity uninterruptible power supply system is not required, whereby the power supply apparatus for a detector can be constructed at low cost. The abnormal stopping process is carried out automatically when the control device determines that an abnormality has occurred, and thus a manual operation is not required.

DESCRIPTION OF REFERENCES

Figure 1:
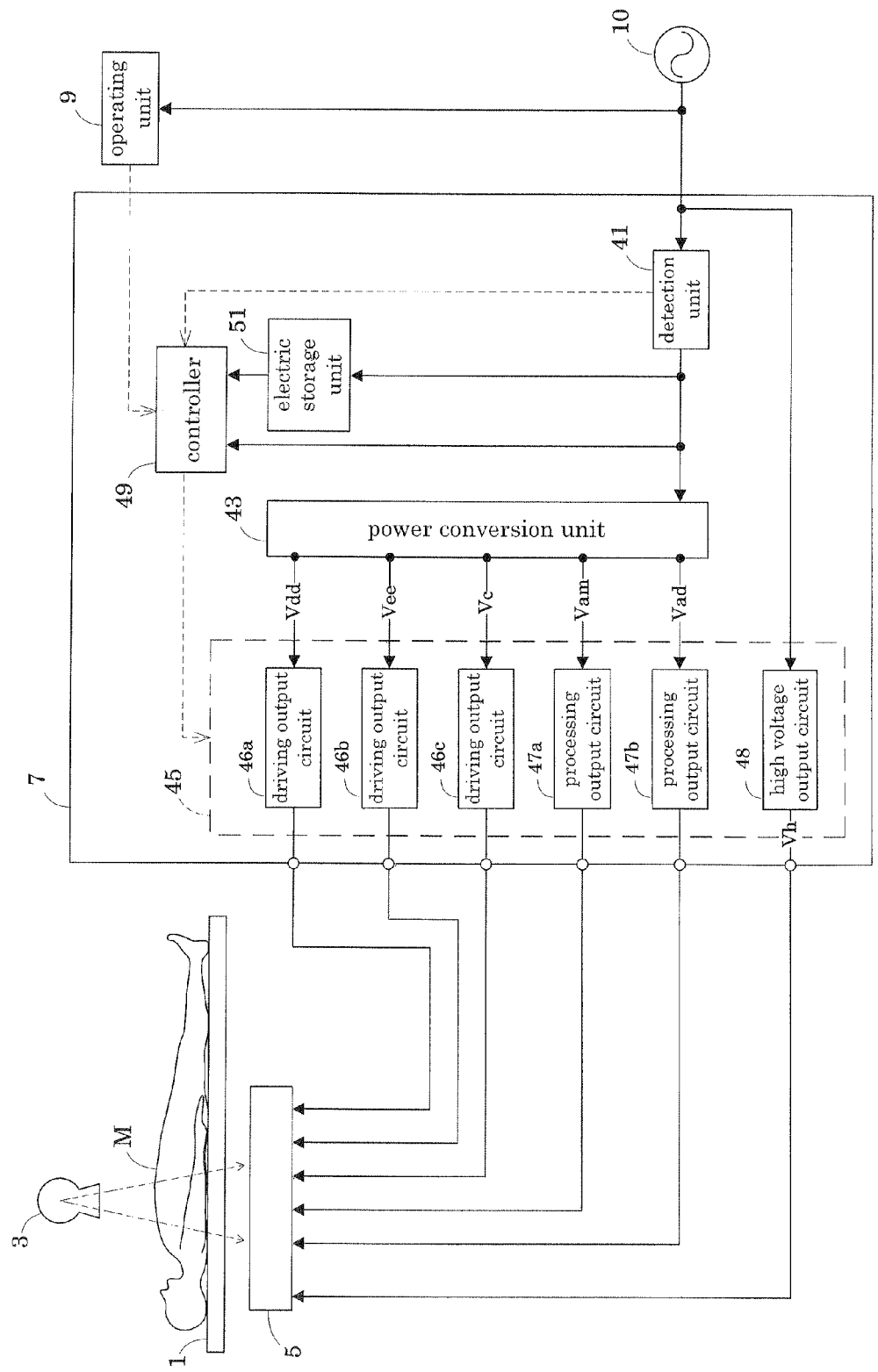
FIG. 1 is a schematic outline view of an X-ray apparatus according to an embodiment.

5 . . . flat panel X-ray detector (FPD)
7 . . . power supply apparatus
10 . . . utility power source
11 . . . semiconductor layer
13 . . . application electrode
15 . . . active matrix substrate
21 . . . integrated circuits (ICs)
$21c$ . . . drive circuit
23 . . . driving printed circuit board
$23c$ . . . drive control circuit
25 . . . integrated circuits (ICs)
$25c$ . . . amplifier circuits
27 . . . processing printed circuit board
$27c$ . . . analog-to-digital converter
41 . . . detection unit
43 . . . power conversion unit
45 power output unit
49 . . . controller
51 . . . electric storage unit
M . . . patient
s . . . switching elements
Vdd ON-state voltage power supply
Vee OFF-state voltage power supply
Vc . . . controlling power supply
Vam . . . amplification power supply
Vad . . . A/D conversion power supply

BEST MODE FOR CARRYING OUT THE INVENTION

In a power supply apparatus for a detector, for providing a plurality of power supplies for a light or radiation detecting detector having a semiconductor layer for converting light or radiation information into charge information, an active matrix substrate having a plurality of switching elements for reading the charge information from the semiconductor layer, and a driving device for driving the active matrix substrate for reading, the power supply apparatus for a detector comprises a power output device capable of individually outputting the plurality of power supplies to be provided for the detector; a detection device for detecting a power supply state of a utility power source for operating the apparatus; a control device for carrying out an abnormal stopping process to stop the power supplies at the power output device in a predetermined order upon determination based on a result of detection by the detection device that an abnormality has occurred; and an electric storage device for supplying electric power to the control device, when the control device determines that an abnormality has occurred, to permit the control device to carry out the abnormal stopping process. This fulfills the object to protect the detector even when a state of electric power supply from a utility power source becomes abnormal, without requiring a large-capacity uninterruptible power supply system.

[Embodiment]

An embodiment of this invention will be described hereinafter with reference to the drawings. FIG. 1 is a schematic outline view of an X-ray apparatus according to the embodiment.

The X-ray apparatus in the embodiment has, applied thereto, a power supply apparatus for a detector, and a light or radiation detection system having the same, according to this invention. This apparatus is an apparatus for X-raying a patient M in the medical field. This apparatus includes a top board 1, an X-ray tube 3 and a flat panel X-ray detector (hereinafter simply called "FPD") 5. The patient M is placed on the top board 1. The top board 1 is formed of an X-ray transmissive material, for example. The X-ray tube 3 and FPD 5 are opposed to each other across the top board 1. The X-ray tube 3 emits X-rays to the patient M. The FPD 5 detects X-rays transmitted through the patient M. The FPD 5 corresponds to the detector in this invention.

A power supply apparatus 7 is connected to the FPD 5. The power supply apparatus 7 is constructed capable of outputting a plurality of power supplies (described hereinafter) individually to the FPD 5. An operating unit 9 is connected to the power supply apparatus 7. The operating unit 9 is formed of a computer having an input device such as a keyboard. When the user operates this operating unit 9, the operating unit 9 receives instructions for starting and stopping the FPD 5, for example. The instructions received are outputted to the power supply apparatus 7. A utility power source 10 is connected to these power supply apparatus 7 and operating unit 9. The utility power source 10 is a commercial power source (AC100V), for example. The utility power source 10 supplies electric power to the power supply apparatus 7 and operating unit 9 for operation. The power supply apparatus 7 corresponds to the power source for a detector in this invention. The power supply apparatus 7 and FPD 5 correspond to the light or radiation detection system in this invention.

Figure 2:
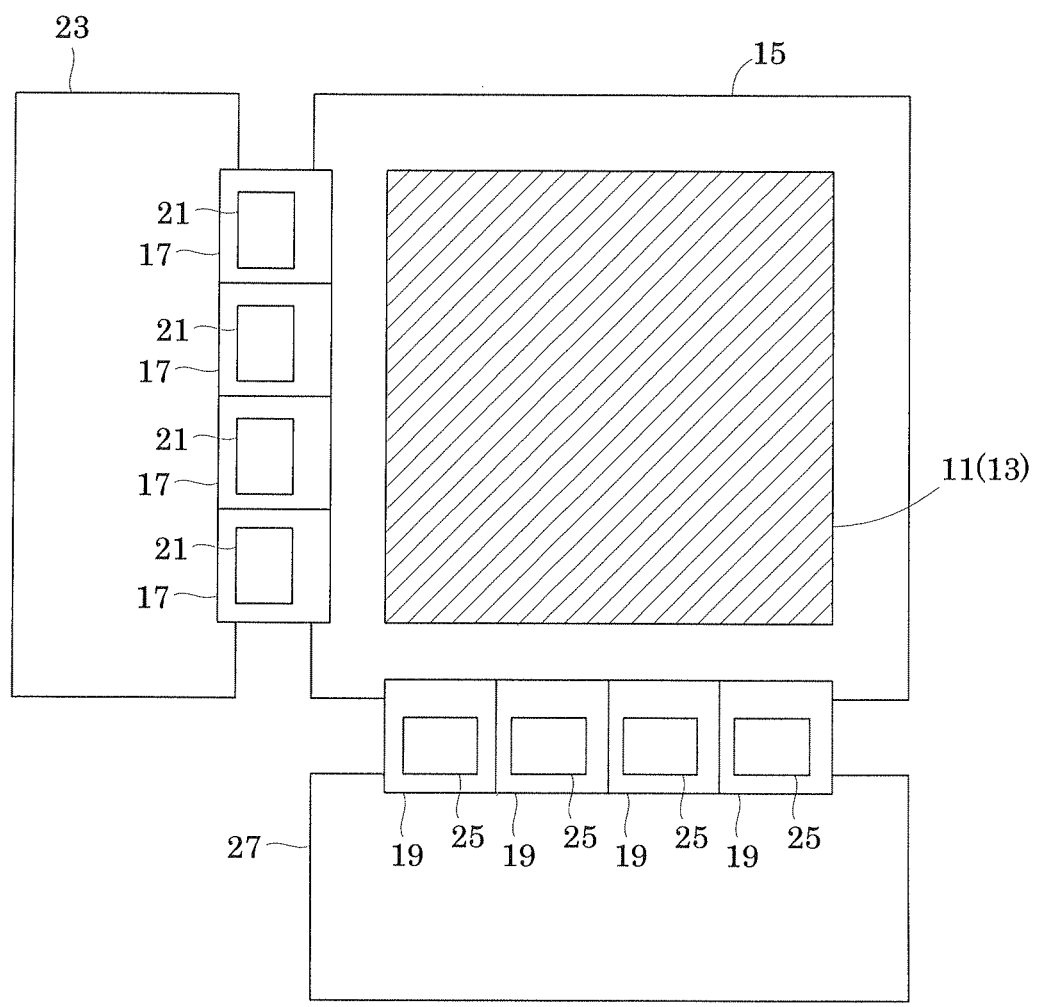
FIG. 2 is a plan view showing a principal portion of an FPD.
Figure 3:
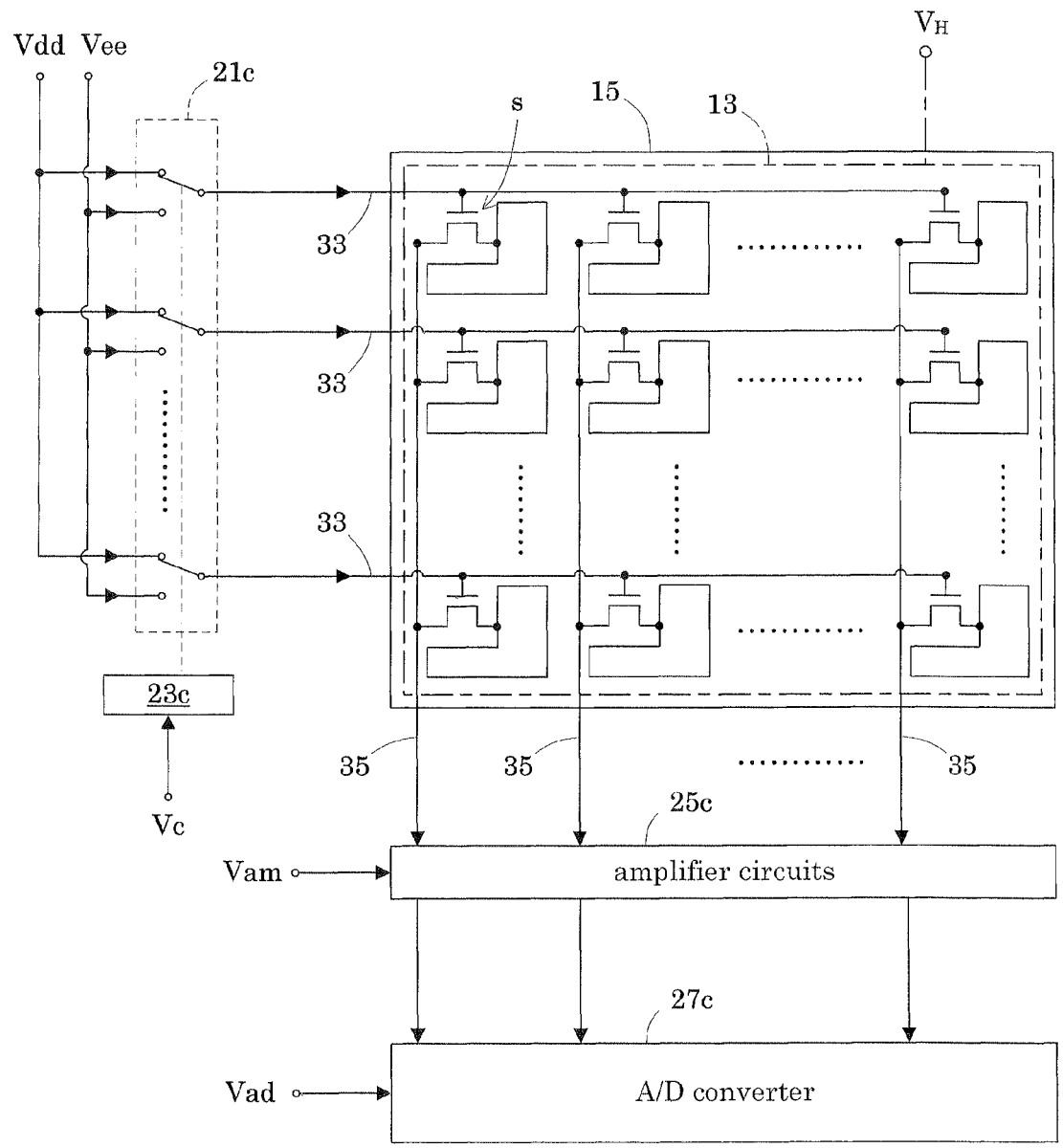
FIG. 3 is a view schematically showing an equivalent circuit of the principal portion of the FPD.
Figure 4:
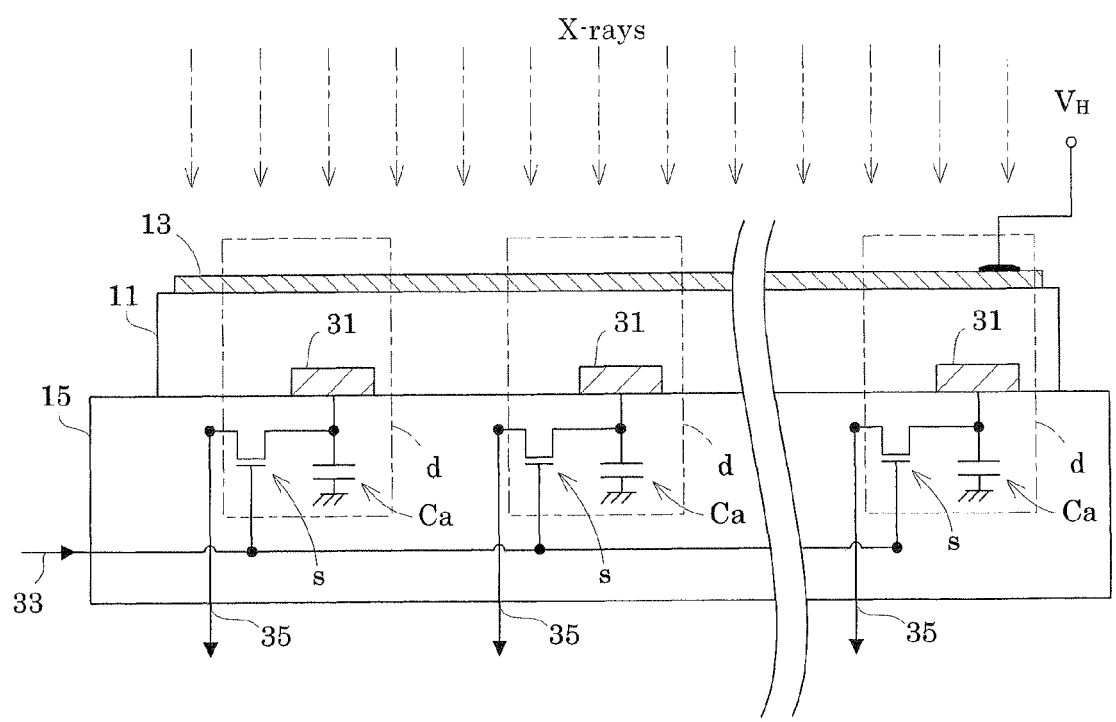
FIG. 4 is a schematic view showing an equivalent circuit of an active matrix substrate as corresponding to its section.
Figure 5:
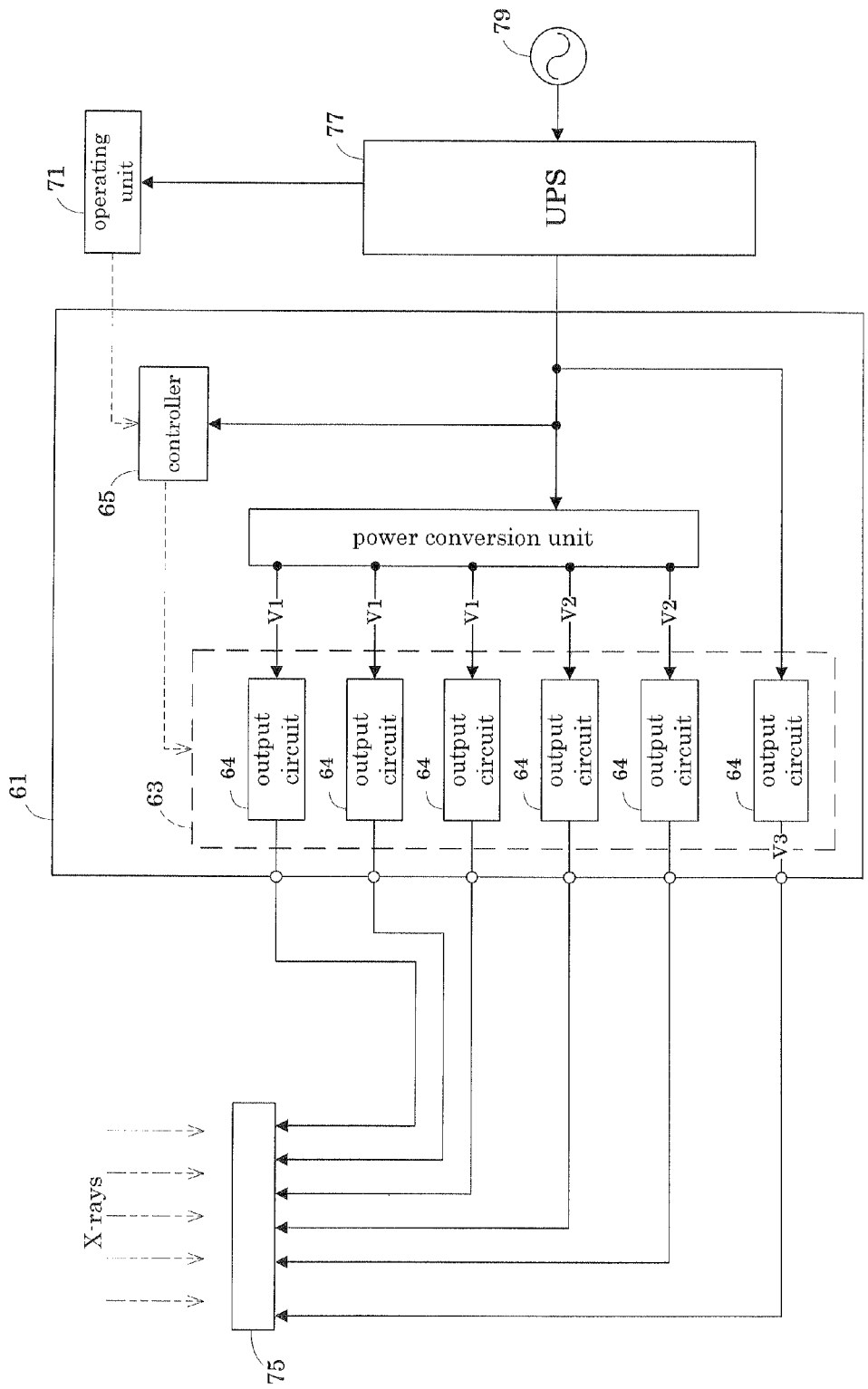
FIG. 5 is a view showing an outline construction of a power supply apparatus in a conventional example.

The FPD 5 will be described with reference to FIG. 2 through FIG. 4. FIG. 2 is a plan view showing a principal portion of the FPD. FIG. 3 is a view schematically showing an equivalent circuit of the principal portion of the FPD. FIG. 4 is a schematic view showing an equivalent circuit of an active matrix substrate as corresponding to its section.

As shown, the FPD 5 is the direct conversion type and includes a semiconductor layer 11 for directly converting X-ray information into charge information. The semiconductor layer 11 is formed of amorphous selenium (a-Se), for example. An application electrode 13 for applying a high voltage to the semiconductor layer 11 is laminated on an X-ray incident surface of the semiconductor layer 11. An active matrix substrate 15 is formed on the back surface of the semiconductor layer 11. The active matrix substrate 15 has a plurality of switching elements s as described hereinafter, to read the charge information converted by the semiconductor layer 11.

Driving flexible substrates 17 are connected to one side of the active matrix substrate 15. Processing flexible substrates 19 are connected to another side. Integrated circuits (ICs) 21 are mounted on the driving flexible substrates 17. These integrated circuits 21 constitute a drive circuit 21c for switching provision and stopping of ON-state voltage power supply Vdd which sets the switching elements s to ON state. More particularly, ON-state voltage power supply Vdd and OFF-state voltage power supply Vee are inputted to the drive circuit, and the drive circuit 21c is constructed capable of selectively outputting these ON-state voltage power supply Vdd and OFF-state voltage power supply Vee. Here, the OFF-state voltage power supply Vee sets the switching elements s to OFF state. The other ends of the driving flexible substrates 17 are connected to a driving printed circuit board 23. A drive control circuit 23c is formed on the driving printed circuit board 23 for controlling switching of the drive circuit 21c. A controlling power supply Vc is inputted to this drive control circuit 23c. The drive control circuit 23c outputs to the drive circuit 21c a signal for controlling switching of the drive circuit 21c. The driving flexible substrates 17, integrated circuits 21 (drive circuit 21c) and driving printed circuit board 23 (drive control circuit 23c) correspond to the driving device in this invention.

Integrated circuits (ICs) 25 are mounted also on the processing flexible substrates 19. Each integrated circuit 25 acts as an amplifier circuit 25c for amplifying the charge information read from the active matrix substrate 15. An amplification power supply Vam is inputted to this amplifier circuit 25c. The other ends of the processing flexible substrates 19 are connected to a processing printed circuit board 27. An analog-to-digital converter 27c is formed on the processing printed circuit board 27 for digitizing output (analog) of the amplifier circuits 25c. An A/D conversion power supply Vad is inputted to the analog-to-digital converter 27c. The processing flexible substrates 19, integrated circuits 25 (amplifier circuits 25c) and processing printed circuit board 27 (analog-to-digital converter 27c) correspond to the processing device in this invention. The analog-to-digital converter 27c corresponds to the analog-to-digital conversion circuit in this invention.

The active matrix substrate 15 will be described further. The active matrix substrate 15 is a transparent glass substrate having electrical insulation property. The active matrix substrate 15 has, formed thereon, a plurality of split electrodes 31 for collecting the charge information converted by the semiconductor layer 11. The split electrodes 31 are separated and arranged along rows and columns which are the two crossing axial directions. A capacitor Ca is connected to each split electrode 31 for storing the charge information. The switching elements s are connected to respective pairs of split electrode 31 and capacitor Ca. The switching elements s are formed of thin film transistors, for example. One set of these split electrode 31, capacitor Ca and switching element s, combined with each site of the semiconductor layer 11 and application electrode 13 corresponding thereto, constitute one detecting element d.

Further, the active matrix substrate 15 has a gate line 33 laid for each row of detecting elements d, and a data line 35 laid for each column of switching elements s. Each gate line 33 is connected commonly to the gates of the switching element s in each row. The other ends of the gate lines 33 are electrically connected to the driving flexible substrates 17, and are drawn out of the active matrix substrate 15. Each data line 35 is connected commonly to the drains of the switching elements s in each column. The other ends of the data lines 35 are electrically connected to the processing flexible substrates 19, and are drawn out of the active matrix substrate 15.

The FPD 5 constructed in this way operates as follows. When X-rays are emitted in a state of the high voltage being applied to the application electrode 13, the semiconductor layer 11 converts the emitted X-rays (X-ray information) to the charge information. While the drive circuit 21c provides OFF-state voltage power supply Vee for the switching elements s under control of the drive control circuit 23c, the switching elements s remain in OFF state. Therefore, the charge information converted by the semiconductor layer 11 is stored in the capacitors Ca. When ON-state voltage power supply Vdd is outputted to one gate line 33 from the drive circuit 21c under control of the drive control circuit 23c, the switching elements s connected to the gate line 33 will be turned on en bloc. Then, the charge information stored in each capacitor Ca is read to the data lines 35 via each switching element s. The read charge information is amplified by each amplifier circuit 25c. The analog information amplified by each amplifier circuit 25c is digitized by the analog-to-digital converter 27c. The digitized information is further subjected to various processes to become X-ray images.

Next, details of the power supply apparatus 7 will be described. The power supply apparatus 7 includes a detection unit 41, a power conversion unit 43, a power output unit 45, a controller 49 and an electric storage unit 51. The detection unit 41 detects voltage of the electric power supplied from the utility power source 10, and outputs a detection result to the controller 49. The power conversion unit 43 converts the electric power supplied from the utility power source 10 to direct current and to a predetermined voltage. And it outputs ON-state voltage power supply Vdd, OFF-state voltage power supply Vee, controlling power supply Vc, amplification power supply Vam and A/D conversion power supply Vad noted hereinbefore. This power conversion unit 43 is realized, as appropriate, by an AC-DC conversion circuit or DC-DC conversion circuit, a filter, a feedback circuit or the like.

Here, ON-state voltage power supply Vdd, OFF-state voltage power supply Vee and controlling power supply Vc are all for driving the active matrix substrate 15 and reading the charge information, and will be called "driving power supplies" as appropriate. Amplification power supply Vam and AID conversion power supply Vad are for processing the charge information read from the active matrix substrate 15, and will be called "processing power supplies" as appropriate. Further, each driving power supply and each processing power supply are direct-current power supplies of low voltage (several tens of volts or less), which will be called collectively "low voltage power supplies". Among the low voltage power supplies, the voltage of ON-state voltage power supply Vdd is the highest.

The power output unit 45 has driving output circuits 46a, 46b and 46c for switching output and stopping of the driving power supplies (Vdd, Vee, Vc) obtained from the power conversion unit 43. It has also processing output circuits 47a and 47b for switching output and stopping of the processing power supplies (Vam, Vad) obtained from the power conversion unit 43. The driving output circuits 46a, 46b . . . , when not distinguished, will be referred to hereinafter as driving output circuits 46. Similarly, the processing output circuits 47a and 47b, when not distinguished, will be referred to hereinafter as processing output circuits 47. Each driving output circuit 46 and each processing output circuit 47 are formed of relays arranged on lines of low voltage power supplies for opening and closing the lines. Further, the power output unit 45 has a high voltage output circuit 48. The high voltage output circuit 48 is formed of a booster circuit (not shown) for converting the electric power supplied from the utility power source 10 to direct-current high voltage, and a voltage varying part (not shown) for varying the voltage boosted by this booster circuit. The high voltage output circuit 48 outputs high voltage power supply Vh. The voltage of high voltage power supply Vh is about several 100 V to several 10 kV. High voltage power supply Vh outputted is provided for the application electrode 13 noted hereinbefore.

The controller 49 controls the power output unit 45. Specifically, it controls each of the driving and processing output circuits 46 and 47 and the high voltage output circuit 48. Thus, the controller 49 causes the various power supplies to be outputted in a predetermined order to start the FPD 5 (starting process). The FPD 5 is stopped by stopping output of the various power supplies in a predetermined order (stopping process). Further, a comparison is made between a result of detection by the detection unit 41 and a reference value set beforehand, to determine whether or not the power supply state of the utility power source 10 is abnormal. When the controller 49 determines that it is abnormal, the FPD 5 is stopped by stopping output of the various power supplies in a predetermined order (abnormal stopping process). Each predetermined order noted above is set beforehand according to the starting, stopping or abnormal stopping. Such controller 49 is realized by a storage medium such as a fixed disk which stores a program specifying the predetermined orders according to starting, stopping and abnormal stopping and a variety of information such as the reference value for comparison with detection results, a central processing unit (CPU) which performs various processes based on this program, and a RAM (Random-Access Memory) used as workspace for arithmetic processes and the like.

The electric storage unit 51 accumulates the electric power supplied from the utility power source 10 at normal times when the power is supplied at a predetermined voltage from the utility power source 10. When the controller 49 determines that an abnormality has occurred, the electric storage unit 51 supplies power to the controller 49. This electric storage unit 51, preferably, is an electric double layer capacitor. The electric double layer capacitor is also called a super capacitor. The capacitance of the electric double layer capacitor is designed or selected to be capable of continuing to supply power to the controller 49 over a time required for the abnormal stopping process. Specifically, at least 1000 µF is preferred.

Next, operation of the X-ray apparatus according to Embodiment 1, particularly the three operations, i.e. starting, stopping and abnormal stopping of the FPD 5, will be described.

<Starting>

It is assumed that the power supply apparatus 7 and operating unit 9 are in operation with electric power supplied from the utility power source 10 to the power supply apparatus 7 and operating unit 9. The user inputs startup instructions to the operating unit 9. The operating unit 9 receives the startup instructions and gives the received startup instructions to the controller 49. The power conversion unit 43 converts the electric power supplied from the utility power source 10, and outputs each low voltage power supply. The controller 49 controls the power output unit 45 to first output OFF-state voltage power supply Vee, controlling power supply Vc and processing power supplies (Vam, Vad). As a result, OFF-state voltage power supply Vee is provided for the drive circuit 21c, and controlling power supply Vc is provided for the drive control circuit 23c. Further, a signal for controlling switching of the drive circuit 21c is inputted from the drive control circuit 23c to the drive circuit 21c. Amplification power supply Vam is provided for the amplifier circuits 25c, and A/D conversion power supply Vad is provided for the analog-to-digital converter 27c. Then, the controller 49 controls the power output unit 45 to output ON-state voltage power supply Vdd. As a result, ON-state voltage power supply Vdd is provided for the drive circuit 21c. Finally, the controller 49 controls the power output unit 45 to output high voltage power supply Vh. As a result, high voltage power supply Vh is provided for the application electrode 13. This completes starting of the FPD 5.

After the FPD 5 is started, an operation by the user causes the X-ray tube 3 to emit X-rays to the patient M, and causes the FPD 5 to detect X-rays transmitted through the patient M. X-ray images of the patient M are created based on detection results of the FPD 5. In this way, X radiography of the patient M is carried out as appropriate.

<Stopping>

The user inputs stop instructions to the operating unit 9. The operating unit 9 receives the stop instructions, and gives them to the controller 49. The controller 49 controls the power output unit 45 to stop the output of high voltage power supply Vh first. This results in a state where high voltage power supply Vh is not applied to the application electrode 13. Then, the controller 49 controls the power output unit 45 to stop the output of ON-state voltage power supply Vdd. As a result, the provision of ON-state voltage power supply Vdd for the drive circuit 21c is stopped. Finally, the controller 49 controls the power output unit 45 to stop the output of each of OFF-state voltage power supply Vee, controlling power supply Vc and processing power supplies (Vam, Vad). As a result, the provision of OFF-state voltage power supply Vee for the drive circuit 21c is stopped, and the provision of controlling power supply Vc for the drive control circuit 23c is stopped. This also stops the signal given from the drive control circuit 23c to the drive circuit 21c. The provision of amplification power supply Vam for the amplifier circuits 25c and the provision of A/D conversion power supply Vad for the analog-to-digital converter 27c are also stopped. This completes stopping of the FPD 5.

<Abnormal Stopping>

It is assumed that the FPD 5 is in operation. The detection unit 41 detects the supply voltage of the utility power source 10, and outputs it to the controller 49. The controller 49 determines whether an abnormality has occurred, from the result of a comparison of the detection result with the reference value. When a power failure or instantaneous interruption occurs to lower the supply voltage of the utility power source 10 below the reference value, the controller 49 determines that an abnormality has occurred. In this case, in place of the utility power source 10, the electric storage unit 51 begins to supply power to the controller 49. The controller 49 controls the power output unit 45 to stop the output of high voltage power supply Vh first. When the output of high voltage power supply Vh has been stopped, the output of ON-state voltage power supply Vdd is stopped next. When the output of ON-state voltage power supply Vdd has been stopped, the output of each of OFF-state voltage power supply Vee, controlling power supply Vc and processing power supplies (Vam, Vad) is stopped finally. The FPD 5 is stopped by the controller 49 carrying out such a series of abnormal stopping steps.

The time from when the controller 49 determines that an abnormality has occurred until the abnormal stopping process is completed is relatively short. Since the power conversion unit 43 has an AC-DC conversion circuit or DC-DC conversion circuit, the voltage of the various low voltage power supplies outputted from the power conversion unit 43 is maintained for a relatively short period even when the supply voltage of the utility power source 10 falls. Therefore, even when the supply voltage of the utility power source 10 falls, the various power supplies successively stop in the predetermined order according to the abnormal stopping process.

Thus, the X-ray apparatus according to the embodiment, with the power supply apparatus 7 having the detection unit 41, can conveniently detect the power supply state of the utility power source 10. Since the detection result of the detection unit 41 is directly inputted to the controller 49, the controller 49 can conveniently determine whether the power supply state is abnormal or not. When an abnormality is found, the electric storage unit 51 supplies power to the controller 49 whereby the controller 49 can carry out the abnormal stopping process reliably. That is, the various power supplies provided for the FPD 5 can be stopped successively in the predetermined order. Consequently, damage or breaking of each circuit of the FPD 5 can be prevented conveniently.

Specifically, in the abnormal stopping process, the drive circuit 21c and drive control circuit 23c can be protected conveniently by stopping the provision of ON-state voltage power supply Vdd having the highest voltage among the driving power supplies (Vdd, Vee, Vc), before the other driving power supplies (Vee, Vc). Particularly where specifications of the integrated circuits (ICs) 21 forming the drive circuit 21c provide that the other power supplies should be stopped after stopping ON-state voltage power supply Vdd when stopping the plurality of power supplies to these integrated circuits (ICs) 21, the integrated circuits (ICs) 21 can be protected effectively.

Each circuit of the FPD 5 can be enhanced more reliably by stopping the provision of ON-state voltage power supply Vdd before the processing power supplies (Vam, Vad) in the abnormal stopping process.

Further, the switching elements s can be protected conveniently by stopping the provision of high voltage power supply Vh before the low voltage power supplies (Vdd, Vee, Vc, Vam, Vad) in the abnormal stopping process. In this connection, when high voltage power supply Vh is provided even after the provision of the low voltage power supplies is stopped, there occurs a possibility that the potential of the switching elements s increases to destroy the switching elements s. The abnormal stopping process in this embodiment can officially prevent such destruction of the switching elements s.

Since the electric storage unit 51 in this embodiment may accumulate only the power consumed by the controller 49 in carrying out the abnormal stopping process, the capacity of the electric storage unit 51 can be made very small.

Thus, it is unnecessary to provide a large-capacity uninterruptible power supply system as in the conventional example. Therefore, the power supply apparatus 7 can be made compact, and the manufacturing cost of the power supply apparatus 7 can be reduced.

The electric storage unit 51 in this embodiment, which is formed of an electric double layer capacitor, can be charged and discharged quickly. The electric double layer capacitor can be charged and discharged only by time constant, and does not require a special circuit for charging and discharging unlike a battery. Thus, the circuit of the electric storage unit 51 can be constructed simply and easily. Since the electric double layer capacitor has a long life, it can improve maintainability of the power supply apparatus 7.

Since the detection unit 41 in this embodiment detects the voltage of the utility power source 10, it can conveniently detect abnormalities such as a power failure and instantaneous interruption that lower the voltage of the utility power source 10.

The controller 49 can appropriately determine whether or not the power supply state of the utility power source 10 is abnormal by comparing the predetermined reference value and detection results of the detection unit 41.

Since the controller 49 automatically carries out the abnormal stopping process when it determines that an abnormality has occurred, a manual operation such as the user operating the operating unit 9 is not required. The X-ray apparatus in this embodiment, preferably, is a special-purpose machine for radiography. Since the X-ray apparatus is not continuously used such as in a surgical operation, insertion of a catheter or IVR if it is a special-purpose machine for radiography, the controller 49 can automatically carry out the abnormal stopping process without causing any inconvenience. However, the X-ray apparatus is not limited to use as a special-purpose machine for radiography, but may have various uses.

This invention is not limited to the foregoing embodiment, but may be modified as follows:

(1) In the foregoing embodiment, the electric storage unit 51 is exemplified by an electric double layer capacitor, but is not limited thereto. A modification may be made to form the electric storage unit 51 with a battery, for example. The electric double layer capacitor has been described as preferably having a capacity of at least 1000 µF, but this is not limitative. A design change can be made to less than 1000 µF as appropriate.

(2) In the foregoing embodiment, ON-state voltage power supply Vdd, amplification power supply Vam, high voltage power supply Vh and so on have been given by way of example. The types and number of power supplies may be varied as appropriate.

(3) In the foregoing embodiment, the abnormal stopping process has been described without particularly stating a relationship in the order of timing for stopping the output of OFF-state voltage power supply Vee, controlling power supply Vc and processing power supplies (Vam, Vad). These may be stopped at the same time, or may be stopped successively in an appropriate order. A modification may be made to stop the provision of ON-state voltage power supply Vdd and processing power supplies (Vam, Vad) at the same time. In this case also, the drive circuit 21c can be protected appropriately since the processing power supplies (Vam, Vad) have little influence on the drive circuit 21c.

(4) In the abnormal stopping process in the foregoing embodiment, the provision of ON-state voltage power supply Vdd is stopped before the other driving power supplies (Vee, Vc), but this is not limitative. For example, when there is a different driving power supply with the highest voltage among the plurality of driving power supplies, the provision of the driving power with the highest voltage may be stopped before the other driving power supplies.

(5) In the foregoing embodiment, the FPD 5 is the direct conversion type having the semiconductor layer 11 for converting radiation information into charge information, but this is not limitative. A change may be made to the indirect conversion type as appropriate. That is, a change may be made in which a conversion layer such as a scintillator converts incident radiation into light information, and a light sensitive semiconductor layer converts the light information into charge information.

(6) In the foregoing embodiment, the FPD 5 detects X-rays, but this is not limitative. For example, radiation or light other than X-rays may be detected.

(7) In the foregoing embodiment, the X-ray apparatus is for use in the medical field, but this is not limitative. For example, it is applicable also to radiographic apparatus for use in industrial fields such as nondestructive testing, RI (Radio isotope) inspection and optical inspection, or in the nuclear field. In each embodiment, reference is made to the patient M, but the patient M is not limited to the human body.

The invention claimed is:

1. A power supply apparatus for a detector, for providing a plurality of power supplies for a light or radiation detecting detector having a semiconductor layer for converting light or radiation information into charge information, an active matrix substrate having a plurality of switching elements for reading the charge information from the semiconductor layer, and a driving device for driving the active matrix substrate for reading, the power supply apparatus comprising:

a power output device capable of individually outputting the plurality of power supplies to be provided for the detector;
a detection device for detecting a power supply state of a utility power source for operating the apparatus;
a control device for carrying out an abnormal stopping process to stop the power supplies at the power output device in a predetermined order upon determination based on a result of detection by the detection device that an abnormality has occurred; and
an electric storage device for supplying electric power to the control device, when the control device determines that an abnormality has occurred, to permit the control device to carry out the abnormal stopping process;
wherein
the power supplies the power output device is capable of individually outputting include a plurality of driving power supplies to be provided for the driving device; and
in the abnormal stopping process, a driving power supply of highest voltage among the driving power supplies is stopped before the other driving power supplies.

2. The power supply apparatus for a detector according to claim 1, wherein the electric storage device is capable of continuing to supply electric power to the control device at least over a time required for the abnormal stopping process.

3. The power supply apparatus for a detector according to claim 1, wherein the time required for the abnormal stopping process is at most one second.

4. The power supply apparatus for a detector according to claim 1, wherein the electric storage device is capable of storing electric power to be consumed by the control device at least during the abnormal stopping process.

5. The power supply apparatus for a detector according to claim 1, wherein the electric storage device is an electric double layer capacitor.

6. The power supply apparatus for a detector according to claim 5, wherein the electric double layer capacitor has a capacitance of at least 1000 µF.

7. The power supply apparatus for a detector according to claim 1, wherein the detection device is arranged to detect a voltage of the utility power source.

8. The power supply apparatus for a detector according to claim 1, wherein the control device is arranged to determine that an abnormality has occurred, when the voltage detected by the detection device falls below a reference value.

9. The power supply apparatus for a detector according to claim 1, wherein:
the power supplies the power output device is capable of individually outputting include a high voltage power supply for applying a high voltage to the semiconductor layer; and
in the abnormal stopping process, the high voltage power supply is stopped first among the power supplies the power output device is capable of individually outputting.

10. A light or radiation detection system comprising:
a detector for detecting light or radiation; and
a power supply apparatus for a detector, for providing a plurality of power supplies for the detector:
wherein the detector includes:
a semiconductor layer for converting light or radiation information into charge information;
an active matrix substrate having a plurality of switching elements for reading the charge information from the semiconductor layer; and
a driving device for driving the active matrix substrate for reading;

wherein the power supply apparatus for a detector includes:
a power output device capable of individually outputting, the plurality of power supplies to be provided for the detector;
a detection device for detecting a power supply state of a utility power source for operating the apparatus:
a control device for carrying out an abnormal stopping process to stop the power supplies at the power output device in a predetermined order upon determination based on a result of detection by the detection device that an abnormality has occurred; and
an electric storage device for supplying electric power to the control device, when the control device determines that an abnormality has occurred, to permit the control device to carry out the abnormal stopping process;
wherein the driving device includes:
a drive circuit for switching provision and stopping of an ON-state voltage power supply to the switching elements; and
a drive control circuit for controlling switching of the drive circuit; and
wherein the drive circuit comprises integrated circuits; and specifications of the integrated circuits provide that the other power supplies should be stopped after stopping the ON-state voltage power supply when stopping the plurality of power supplies to the integrated circuits.

11. The light or radiation detection system according to claim 10, wherein the light or radiation detection system is used exclusively for radiography.

12. A power supply apparatus for a detector, for providing a plurality of power supplies for a light or radiation detecting detector having a semiconductor layer for converting light or radiation information into charge information, an active matrix substrate having a plurality of switching elements for reading the charge information from the semiconductor layer, and a driving device for driving the active matrix substrate for reading, the power supply apparatus comprising:
a power output device capable of individually outputting the plurality of power supplies to be provided for the detector;
a detection device for detecting a power supply state of a utility power source for operating the apparatus;
a control device for carrying out an abnormal stopping process to stop the power supplies at the power output device in a predetermined order upon determination based on a result of detection by the detection device that an abnormality has occurred; and
an electric storage device for supplying electric power to the control device, when the control device determines that an abnormality has occurred, to permit the control device to carry out the abnormal stopping process;
wherein:
the power supplies the power output device is capable of individually outputting include a plurality of driving power supplies to be provided for the driving device;
the driving power supplies further include an ON-state voltage power supply for applying an ON-state voltage to set the switching elements to ON state; and
in the abnormal stopping process, the ON-state voltage power supply is stopped before the other driving power supplies.

13. The power supply apparatus for a detector according to claim 12, wherein the ON-state voltage of the ON-state voltage power supply is higher than voltages of the other driving power supplies.

14. The power supply apparatus for a detector according to claim 12, wherein:
the driving device includes a drive circuit for switching provision and stopping of the ON-state voltage power supply for the switching elements, and a drive control circuit for controlling switching of the drive circuit;
the ON-state voltage power supply is inputted to the drive circuit; and
the other driving power supplies are inputted to one of the drive circuit and the drive control circuit.

15. The power supply apparatus for a detector according to claim 14, wherein the drive circuit comprises integrated circuits.

16. The power supply apparatus for a detector according to claim 15, wherein specifications of the integrated circuits provide that the other power supplies should be stopped after stopping the ON-state voltage power supply when stopping the plurality of power supplies to the integrated circuits.

17. The power supply apparatus for a detector according to claim 12, wherein:
the detector includes a processing device for processing the charge information read by the active matrix substrate;
the power supplies the power output device is capable of individually outputting include a plurality of processing power supplies to be provided for the processing device; and
in the abnormal stopping process, the ON-state voltage power supply is stopped before all the processing power supplies.

18. The power supply apparatus for a detector according to claim 17, wherein:
the processing device includes at least amplifier circuits for amplifying the charge information, and an analog-to-digital converter circuit for digitizing output of the amplifier circuits; and
the processing power supplies are inputted to the amplifier circuits and the analog-to-digital converter circuit, respectively.

19. The power supply apparatus for a detector according to claim 12, wherein the electric storage device is capable of continuing to supply electric power to the control device at least over a time required for the abnormal stopping process.

20. The power supply apparatus for a detector according to claim 12, wherein the time required for the abnormal stopping process is at most one second.

21. The power supply apparatus for a detector according to claim 12, wherein the electric storage device is capable of storing electric power to be consumed by the control device at least during the abnormal stopping process.

22. The power supply apparatus for a detector according to claim 12, wherein the electric storage device is an electric double layer capacitor.

23. The power supply apparatus for a detector according to claim 22, wherein the electric double layer capacitor has a capacitance of at least 1000 μF.

24. The power supply apparatus for a detector according to claim 12, wherein the detection device is arranged to detect a voltage of the utility power source.

25. The power supply apparatus for a detector according to claim 12, wherein the control device is arranged to determine that an abnormality has occurred, when the voltage detected by the detection device falls below a reference value.

26. The power supply apparatus for a detector according to claim 12, wherein:

the power supplies the power output device is capable of individually outputting include a high voltage power supply for applying a high voltage to the semiconductor layer; and in the abnormal stopping process, the high voltage power supply is stopped first among the power supplies the power output device is capable of individually outputting.

* * * * *